United States Patent
Arnold et al.

(10) Patent No.: US 6,372,425 B1
(45) Date of Patent: Apr. 16, 2002

(54) LARGE SCALE AFFINITY CHROMATOGRAPHY OF MACROMOLECULES

(75) Inventors: Beth Arnold, Quakertown; Paul M. Keller, Landsale; Anthony J. Conley, Exton; Alan R. Shaw, Doylestown, all of PA (US); Jwu-Sheng Tung, Cranbury, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/140,201

(22) Filed: Aug. 21, 1998

Related U.S. Application Data

(63) Continuation of application No. 08/751,283, filed on Nov. 18, 1996, now abandoned, which is a continuation of application No. 08/329,749, filed on Oct. 26, 1994, now abandoned.

(51) Int. Cl.$^7$ .......................... C12Q 1/70; C12N 15/00; C12P 21/08
(52) U.S. Cl. ............................ 435/5; 435/6; 435/235.1; 435/320.1; 435/DIG. 1; 435/DIG. 2; 435/DIG. 14; 435/DIG. 15; 435/DIG. 40; 530/387.3
(58) Field of Search ................ 435/6.5, 7.1, 235.1, 435/320.1, 172.1, 7.2, 91.1, DIG. 1, DIG. 14, DIG. 15, DIG. 40; 530/387.3

(56) References Cited

U.S. PATENT DOCUMENTS

| | | |
|---|---|---|
| 5,223,409 A | 6/1993 | Ladner et al. |
| 5,403,484 A | 4/1995 | Ladner et al. |
| 5,837,500 A | 11/1998 | Ladner et al. |

OTHER PUBLICATIONS

Djojonegoro, B. et al. "Bacteriophage Surface Display of an Immunoglobulin–binding Domain of *Staphylococcus aureus* Protein A", Bio/Technology, 1994, vol. 12, pp. 169–172.

MacLennan, J. "Engineering Microprotein Ligands for Large–Scale Affinity Purification", Bio/Technology, 1995, vol. 13, pp. 1180–1183.

*Primary Examiner*—Padmashri Ponnaluri
(74) *Attorney, Agent, or Firm*—Anna L. Cocuzzo; Jack L. Tribble

(57) ABSTRACT

A process of purifying target molecules is described that involves the selection of ligands based on identifying, in real time, association and dissociation constants with a given target molecule; using this information to select at least one ligand that exhibit predetermined association and dissociation constants with a given target molecule; anchoring a quantity of ligand to an activated solid support; contacting a quantity of target molecules with the anchored ligand(s); removing low affinity target molecules from anchored ligand and eluting particularly pure target molecules.

10 Claims, No Drawings

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:1:

TCGAAAGCAA GCTGATAAAC CG                                            22

(2) INFORMATION FOR SEQ ID NO:2:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (xi) SEQUENCE DESCRIPTION: SEQ ID NO:2:

ACAGACAGCC CTCATAGTTA GCG                                           23

(2) INFORMATION FOR SEQ ID NO:3:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (xi) SEQUENCE DESCRIPTION: SEQ ID NO:3:

GTAAATGAAT TTTCTGTATG AGG                                           23

(2) INFORMATION FOR SEQ ID NO:4:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (xi) SEQUENCE DESCRIPTION: SEQ ID NO:4:

CCCTCTAGAA ATAATTTTGT TTAACTTTAA GAAGGAGATA TACATATGGC CGACGGGGCT    60

(2) INFORMATION FOR SEQ ID NO:5:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:5:

Ala Asp Gly Ala
1

(2) INFORMATION FOR SEQ ID NO:6:

(i) SEQUENCE CHARACTERISTICS:

(A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO:6:

CTCAGATCTA TTAATGGTGA TGGTGATGAT GTATTTTGTC ACAATCAATA GAAAATTC          58

(2) INFORMATION FOR SEQ ID NO:7:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Cys Asp Lys Ile
1

(2) INFORMATION FOR SEQ ID NO:8:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

His His His His His His
1               5

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Gly Ala Lys Lys Ala Lys
1               5

(2) INFORMATION FOR SEQ ID NO:10:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Leu Leu Arg Thr Ile Met Ile Gly Pro Gly Arg Leu Leu His Ser
1               5                   10                  15

(2) INFORMATION FOR SEQ ID NO:11:

(i) SEQUENCE CHARACTERISTICS:
        (A) LENGTH: 18 amino acids
        (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO:11:

Leu Leu His Arg Arg Asp Ile Gly Pro Ala Arg Thr Arg Glu Ile Gly
1               5                   10                  15

Leu Leu (2) INFORMATION FOR SEQ ID NO:12:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Trp Ser Lys Arg Glu Ser Val Met Phe Gly Pro Gly Arg Gly Thr
1               5                   10                  15

(2) INFORMATION FOR SEQ ID NO:13:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Leu Leu Arg Lys Val Asn Ile Gly Pro Gly Arg Val His Gly Asn Ser
1               5                   10                  15

Leu Leu (2) INFORMATION FOR SEQ ID NO:14:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:14:

Gln His Arg Ala Ala Ser Val His Leu Gly Pro Ser Arg Ala Gly
1               5                   10                  15

(2) INFORMATION FOR SEQ ID NO:15:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:15:

Cys Ser Thr Arg His Leu Gly Pro Gly Arg Val Glu Gly Val Leu Cys
1               5                   10                  15
```

-continued (2) INFORMATION FOR SEQ ID NO:16:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Cys Arg Gln Val Met Leu Gly Pro Gly Arg Gly Asp Arg Leu Glu Cys
1               5                   10                  15

(2) INFORMATION FOR SEQ ID NO:17:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Cys Gly Ala Gly His Val Gly Pro Gly Arg Tyr Gly Ala Leu Ser Cys
1               5                   10                  15

LARGE SCALE AFFINITY CHROMATOGRAPHY OF MACROMOLECULES

This application is a continuation of application Ser. No. 08/751,283, filed on Nov. 18, 1996 now abandoned which is a file wrapper continuation of application Ser. No. 08/329,749, filed on Oct. 26, 1994 now abandoned.

SUMMARY OF THE INVENTION

This invention relates to a process for optimizing ligand-target molecule system selection and using a selected system for preparing large scale quantities of macromolecules in particularly pure form.

BACKGROUND OF THE INVENTION

The production of an array of ligands to select a ligand or a set of ligands for use in a macromolecule purification scheme has traditionally been by organic synthesis methods. Such methods include solid-phase and liquid-phase synthesis. Solid-phase methods are capable of producing longer ligands than liquid-phase methods thus making solid-phase methods preferable. However, ligands produced using either of these methods are difficult to identify and amplify.

Ligand synthesis in a biological system is advantageous over organic synthesis because of the ability to identify and amplify large quantities of ligands. Until recently, biological system synthesis of an array of ligands, such as an epitope library, was limited. However, random peptide libraries that take advantage of the ability of filimentous phage coat protein gene pIII to accept and express foreign DNA on its surface have been described as being useful to identify millions of potential ligands quickly. See, e.g., Scott, J. K. and Smith, G. P., *Science*, 449, 386–390 (1990), Devlin, J. J., et al., *Science*, 449, 404–406 (1990), Cwirla, S. E. et al., *Proc. Nat. Acad. Sci. USA*, 87, 6378–6382 (1990) and U.S. Pat. No. 5,223,409.

Historically, ligand-target molecule system selection for macromolecules have relied upon secondary indication methods to determine appropriate ligands. Such methods include RIA, ELISA, and biotin-avidin complex formation assays. Although these methods identify ligand-target molecule systems that have an unusually high association constants, it is only with subsequent rounds of screening that one skilled in the art can identify ligand-target molecule systems with sufficient binding characteristics for use in subsequent macromolecule purification. These techniques have other deficiencies including the ability to produce false positives, being time consuming and lacking the ability to differentiate between active and nonactive macromolecules during purification.

Surface plasmon resonance (SPR) has been known for quite some time, Kreetschmann, E., & Raether, H., Z. Naturforsch. A23, 2135 (1968). However, it was not until recently that the use of SPR to study ligand-target molecule interactions was described, Karlsonn, R., et al., *J. Immunol. Methods*, 145, 249 (1991).

It is well known that affinity chromatography is an effective purification approach that exploits a macromolecule's biological function. Most macromolecules possess active sites that perform unique functions. These active sites are involved in the recognition and the catalysis of selected small molecules or restricted regions of other macromolecules. It is the property of recognition upon which the principles of affinity chromatography have been developed. The fundamental requirement of affinity chromatography is that the comparative rate constants reflect reasonable affinity, and that the qualitative nature of the ligand and target molecule reflect reasonable stereochemical specificity.

It is desirable that an interacting ligand-target molecule system be chosen such that the ligand-target molecule complex is not chemically altered as a result of the interaction. Many nonenzymatic interacting systems do not exhibit such chemical alteration and are, therefore, ideally suited for affinity chromatography purification. Such interacting systems theoretically include antigens, antibodies, vitamin and drug binding proteins, biological receptors, and transport proteins.

It is also desirable that the interacting ligand-target molecule system be chosen such that the target molecule binds sufficiently fast to the ligand and that the ligand-target molecule system exhibit a sufficiently slow dissociation, thereby allowing large quantities of the target molecule to couple with the ligand without significant loss of target molecules before elution. Following these parameters it is possible to increase the purity and amount of target molecule ultimately recovered.

The aforementioned techniques are themselves individually known. However, the combination of these techniques to identify ligand-target molecule systems with specific association and dissociation constants for subsequent purification of target molecules and the subsequent purification of target molecules using identified ligand-target molecule systems is not known.

ABBREVIATIONS AND DEFINITIONS

The following terms are used herein according to the definitions.

| TERM | DEFINITION |
| --- | --- |
| AIDS | Acquired Immune Deficiency Syndrome |
| HIV | The generic tenn for the presumed etiological agent of AIDS, ARC or both; so referred to as strains HTLV-III, ARV and LAV. |
| Library | A collection of DNA or oligopeptide sequences, of defined length, with or without limited sequence restrictions. |
| Ligand | An oligopeptide that binds target molecules. Ligands may differ one from another in their binding affinities for the target molecule. |
| Macromolecule | Any biologically active compound, including but not limited to antibodies, antigens, proteins, or enzymes. |
| PCR | Polymerase Chain Reaction |
| Recombinant fusion polypeptide (RFP) | Polypeptide or oligopeptide expressed as a contiguous translation product from a spliced foreign DNA in a recombinant eukaryotic or prokaryotic expression system, wherein the spliced foreign DNA is derived from two or more coding sequences of different origin, and joined together by ligation or PCR. |
| Recombinant protein | A polypeptide or oligopeptide expressed by foreign DNA in a recombinant eukaryotic or prokaryotic expression system. |

-continued

| TERM | DEFINITION |
|---|---|
| Recombinant expression system | A cell containing a foreign DNA expressing a foreign protein or a foreign oligopeptide. |
| SPNE | Selected Principle Neutralization Epitope, which is the principle neutralization determinant bound by one or more broadly neutralizing antibodies. SPNE is defined to include consensus sequences. |
| SPR | Surface Plasmon Resonance. |
| Target molecule | Any compound of interest for which a ligand is desired. A target molecule can be any macromolecule. |

The terms "protein," "peptide," "oligopeptide," and "polypeptide" and their plurals will be used interchangeably to refer to chemical compounds having amino acid sequences of five or more amino acids. "Amino acid" refers to any of the 20 common amino acids for which codons are naturally available and are listed in the table of amino acids.

As used herein, all amino acid three letter and single letter designations conform to those designations which are standard in the art, and are listed as follows:

| | | |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When any variable, e.g., SPNE, occurs more than one time in any constituent, its definition on each occurrence is independent of its definition at every other occurrence. Also, combinations of substituents, variables, or both are permissible only if such combinations result in stable compounds.

DETAILED DESCRIPTION OF THE INVENTION

The present invention overcomes the problems of previous methods for identifying specific ligands for the purification of macromolecules. One embodiment of the present invention is to prepare RFPs selected as SPNEs of phage libraries that bind to a specific target molecule. Another embodiment of the present invention is to determine, in real time, the association and dissociation constants for the RFPs and the target molecule of choice and then select RFPs that meet predetermined binding characteristics in order to optimally purify the target molecule. A further embodiment of the present invention is to provide sufficient qualities of identified RFPs for target molecule purification. Yet a further embodiment of the present invention is to use at least one of the identified RFPs as a ligand to obtain large quantities of a target molecule in an active and particularly pure form in an affinity chromatography purification scheme. These and other objects will become apparent to those skilled in the art in the following disclosure.

Expression of SPNE in a Recombinant Expression System

It is now a relatively straight forward technology to prepare cells expressing a foreign gene. Such cells act as hosts and include bacteria, yeast, fungi, plant cells or animal cells. Expression, vectors for many of these host cells have been characterized and are used as starting materials in the construction, through conventional recombinant DNA techniques, of vectors having a foreign DNA insert of interest. Any DNA is foreign if it does not naturally derive from the host cells used to express the DNA insert. The foreign DNA insert may be expressed on extra-chromosomal plasmids after integration in whole or in part of the host cell chromosome(s), or may actually exist in the host cell as a combination of more than one molecular form. The choice of host cell and expression vector for the expression of a desired foreign DNA largely depends on availability of the host cell and how fastidious it is, whether the host cell will support the replication of the expression vector and other factors readily appreciated by those of ordinary skill in the art.

The technology for recombinant prokaryotic expression systems is well developed and reproducible. A typical host cell is *E. coli*. The technology is illustrated by treatises such as Wu, R (ed), *Meth. Enzymol.*, 68 (1979) and Maniatis, T. et al., *Molecular Cloning: A Laboratory Manual*, Cold Spring Harbor (1982) and updates thereof.

The foreign DNA insert of interest is any DNA sequence coding for a SPNE (or fragment thereof of at least 5 amino acids in length) of the present invention, including any synthetic sequence with this coding capacity or any such cloned sequence or combination thereof. For example, SPNE peptides coded and expressed by an entirely recombinant DNA sequence is encompassed by this invention.

Vectors useful for constructing prokaryotic expression systems for the production of recombinant SPNE include the DNA sequence for SPNE, fragment or variant thereof, operatively linked thereto with appropriate transcription activation DNA sequences, such as a promoter, an operator or both. Other typical features include appropriate ribosome binding sites, termination codons, enhancers, terminators and replicon elements. These additional features can be inserted into the vector at the appropriate site or sites by conventional splicing techniques such as restriction endonuclease digestion and ligation.

Yeast expression systems, which are one variety of recombinant eukaryotic expression systems, generally employ *Saccharomyces cerevisiae* as the species of choice for expressing recombinant proteins. *S. cerevisiae* and similar yeasts possess well known promoters useful in the construction of yeast expression systems, including but not limited to GAP491, GAL10, ADH2 and alpha mating factor.

Yeast vectors useful for constructing recombinant yeast expression systems expressing SPNE include, but are not limited to, shuttle vectors, cosmids, chimeric plasmids, and those having sequences derived from 2-micron circle plasmids.

Insertion of the appropriate DNA sequence coding for SPNE, fragment or variant thereof, into these vectors will, in principle, result in a useful recombinant yeast expression system for SPNE where the modified vector is inserted into the appropriate host cell, by transformation or other means.

Recombinant mammalian expression systems are another means of producing the recombinant SPNE of this invention. In general, a host mammalian cell can be any cell that has been efficiently cloned in cell culture. Host mammalian cells useful for the purpose of constructing a recombinant mammalian expression system include, but are not limited to, Veer cells, NIH3t3, COS, murine C127, NSO or mouse L cells. Mammalian expression vectors can be based on virus vectors, plasmid vectors which may have SV40, BPV or other viral replicons, or vectors without a replicon for animal cells. Detailed discussions on mammalian expression vectors can be found in the treatises of Glover, D. M. (ed.) "DNA Cloning: A Practical Approach," IRL (1985), Vols. I and II.

Phage epitope libraries are unusually versatile vehicles for identifying new antigens or ligands. The ability to obtain a phage epitope library that bind to antibodies and other receptors has been described by the following: Scott, J. K. and G. P Smith. "Searching for Peptide Ligands with an Epitope Library". *Science*, 249:386–390, (1990); Devlin, J. J., L. C. Panganiban, and P. E. Devlin. Random Peptide "Libraries: A Source of Specific Protein Binding Molecules". *Science* 249:404–406, (1990); Cwirla, S. E., et al., "Peptides on phage: A vast library of peptides for identifying ligands". *Proc. Natl. Acad. Sci. USA*, 87:6378–6382(1990); and U.S. Pat. No. 5,223,409. Typically, the phage has inserted into its genome a small, randomly generated DNA sequence, e.g., 45 base pairs, which will generate exposed oligopeptide surfaces in the mature phage. Mixing a library of such mature phage with a screening antibody of desired specificity, followed by separation of bound from unbound phage, allows the opportunity to clone and sequence the bound phage. A conventional example of a phage epitope library is the filamentous phage fd and its gene III coding for minor coat protein pIII.

A rapid method of constructing a phage library containing random fifteen amino acid epitopes has been described by Scott, J. K. et al., *Science* 249, 386 (1990). This protocol utilizes synthetic 110 BP BglI fragments which were prepared containing degenerate coding sequence (NNK)15, wherein N stands for an equal mixture of G, A, T and C, and K stands for an equal mixture of G and T. The library is constructed by ligating the synthetic 110 bp BglI fragments in phage. fUSE5 and transfecting *E. coli* cells with the ligation product by electroporation. The resulting phage oligopeptide epitope library has a complexity of approximately $40 \times 10^6$ different epitopes.

Organic Synthesis of SPNE

Standard and conventional methods exist for rapid and accurate synthesis of long peptides on solid-phase supports. Solution-phase synthesis is usually feasible only for smaller peptides.

Synthesis on solid-phase supports, or solid-phase synthesis, is most conveniently performed on an automated peptide synthesizer according to, e.g., Kent S. et al., "Modem Methods for the Chemical Synthesis of Biologically Active Peptides," in Alitalo, K. et al., (eds.). *Synthetic Peptides in Biology and Medicine*, Elsevier 1985, pp. 29–57. Manual solid-phase synthesis may be employed instead, by following the classical Merrifield techniques, as described, e.g., in Merrifield, R. B., *J. Am. Chem. Soc.* 85, 2149 (1963), or known improvements thereof. Solid-phase peptide synthesis may also be performed by the Fmoc methods, which employs very dilute base to remove the Fmoc protecting group. Segment synthesis-condensation is a further variant of organic synthesis of peptides as within the scope of the techniques of the present invention.

In organic synthesis of peptides, protected amino acids are condensed to form amide or peptide bonds with the N-terminus of a growing peptide. Condensation is usually performed with the carbodiimide methods by reagents such as dicyclohexylcorbodiimide or N-ethyl, $N_1$ (λ-methylaminopropyl) carbodiimide. Other methods of forming the amide or peptide bond include, but are not limited to, synthetic routes via and acid chloride, azide, mixed anhydride or activated ester. Common solid-phase supports include polystyrene or polyamide resins.

The selection of protecting groups of amino acid side chains is, in part, by the amino acid and the peptide components involved in the reaction. Such amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butoxycarbonyl (BOC) for protecting the ε-amino group, in part because the BOC protecting group is readily removed by relatively mild acids such as trifluoroacetic acid (TFA) or hydrogen chloride in ethyl acetate.

The OH group of Thr and Ser may be protected by the Bzl (benzyl) group and the ε-amino group of Lys may be protected by the isopropoxycarbonyl (IPOC) group or the 2-chlorobenxyloxycarbonyl (2-Cl-CBZ) group. Treatment with hydrogen fluoride or catalytic hydrogenation are typically employed for removal of IPOC or 2-Cl-CBZ.

For preparing cocktails of closely related peptides, see, e.g., Houghton, R. A., *Proc. Nat. Acad. Sci. USA*, 82, 5131 (1985).

Selection of Desired Phage Epitopes

It is highly desirable to select desired phage epitopes for subsequent screening from a phage library containing about $40 \times 10^6$ epitopes. Several methods are available for screening such a large library; including, but not limited to, biotin-avidin complex formation. The applicants have employed a method for screening phage epitope libraries that involves selection of epitopes by binding a phage expressing a foreign protein on its coat to a solid-phase supported antibody. This method is useful for virtually any antibody, i.e., polyclonal or monoclonal or collection of monoclonals thereto. Any antigen can be screened. The screening method employed by the present invention is illustrated by HIV antigens screened with an HIV specific broadly neutralizing antibody (hereinafter 447 antibody).

Methods of producing 447 antibody may be found in WO 93/08216 (Apr. 29, 1993). More specifically, 447 antibody is a monoclonal antibody identified from a human patient. Human blood specimens donated from HIV-1 positive individuals were the source of peripheral B cells expressing neutralizing antibodies. These cells were immortalized by Epstein-Barr virus (EBV) infection, then individual B cell clones were screened for their ability to secrete antibody which bound a peptide sequence representing the V3 loop of HIV-1 strain MN in a solid phase ELISA format. B cell clones positive in this assay were subsequently stabilized by their fusion to the SHM-D33 cell line (a murine×human heterohybridoma, ATCC CRL 1668). Resultant B cell-heterohybridoma clones were screened for their production of antibody which recognizes the MN V3 loop peptide in a solid-phase ELISA. These procedures establish the criteria for identification and isolation of stable human antibody-producing cells wherein the antibody produced is potentially useful for development into a substance for treatment prophylatically in cases of suspected HIV-1 exposure, and therapeutically in HIV-1 positive individuals.

Screening of mature phage expressing a foreign gene involves two separate methods. First, selection of desired phage epitopes with a solid-phase supported antibody of any desired specificity. The second method, which is optional, relates to identification of desired phage epitopes by antibody lifts.

A. Selection

Selection of desired phage epitopes in a phage epitope library is performed as follows. An essentially pure preparation of antibody is adsorbed or otherwise attached to a solid-phase support, hereinafter also referred to as solid-phase supported Ab. The most preferred embodiment is monoclonal antibody adsorbed to polystyrene beads large enough to be picked up with tweezers, e.g., with a diameter of about 0.25 inch. Such large beads contribute to the ease of subsequent washing steps. Other embodiments include any solid-phase adsorbent for antibody, or any plastic, or glass bead or polysaccharide gel, e.g., SEPHAROSE. Polysaccharide gels are typically covalently conjugated to purified antibody by, e.g., cyanogen bromide.

Incubation of the solid-phase supported Ab with BSA, milk solids or other reagent for blocking non-specific interactions is preferable before selection. The presence of low levels of mild or nonionic detergent is desirable, e.g., 0.5% (v/v) of one or more in the polyoxyethylene (20) sorbitan monoleate series (TWEEN), octylglucopyranoside or Nonidet NP-40. It is apparent to those skilled in the art how to adjust the conditions for coating with such blocking agents.

An appropriate density of antibody should be determined by titration. Applicants have successfully performed selection with a density of about 0.1 $\mu$g 447 antibody/cm$^2$ on polystyrene beads (d=0.25 inch). Densities in the lower range select high affinity epitopes because of the reduced incidence of multivalent binding by the antibody to the multiple copies of the epitope on the phage tip. It is apparent to those skilled in the art how to determine the most suitable density for an antibody preparation, by monitoring the bound phage population. As a general rule, a manageable complexity of bound and eluted phage ranges from about $5 \times 10^3$ to about $10^5$ phage.

Throughout the selection method described below, a wide variation in incubation times, washing times, temperature and pH is covered. It is apparent to those skilled in the art that, given a particular incubation or washing step, a suitable set of variant reaction conditions can be readily ascertained. Applicants have found that temperature and pH are critical in the stringent selection of high affinity epitopes, e.g., temperatures exceeding about 70° C. at neutral pH or exceeding about 38° C. at about pH 4.0, are lethal to the phage. Aside from the critical parameters of temperature and pH, the typical buffer may contain a non-specific blocking agent such as bovine serum albumin (BSA) or milk solids, as well as low levels of a nonionic detergent. For example, TTBS (50 mM Tris, pH 7.5, 150 mM NaCl, 0.5% (v/v) TWEEN-20) in about 1 mg/ml BSA is typical.

Solid-phase supported antibody is first incubated with the epitope phage library to effect binding of the phage epitopes to the antibody. It is preferred to use enough phage to vastly exceed the library complexity, e.g., $10^{11}$ phage, which is 1000 fold more than its complexity of $10^8$. Incubation between about 4° C. and about 65° C., for at least 10 minutes is performed. Applicants typically incubate overnight at about 4° C. Alternatively, a one hour incubation at about 37° C. will select epitopes binding at a fast association rate. Incubation conditions are subject to a wide range of variations, as discussed above, but a neutral buffer containing a non-specific blocking agent is preferred, e.g., TTBS, 1 mg/ml BSA.

Washing the phage-bound solid-phase supported antibody to remove unbound phage is carried out in a variety of conditions, depending on the desired stringency. Generally, the higher the desired stringency, the higher the temperature conditions of washing, up to about 70° C. in some conditions.

For high stringency selection, washing of the bead with bound phage is carried out by washing from about 3 to about 20 times in buffer, e.g., T.T.B.S., at neutral pH at about 65° C. without blocking agent (hereinafter 65° C. wash). Low-affinity phage epitopes are then eluted by washing one or more times by brief (about 2 to 5 minutes) immersion in a mildly acidic buffer without blocking agent (at about pH 3.0 to about pH 5.0 with pH 4.0 being preferred) at about ambient temperature or between about 4° C. and about 37° C. (the pH 4.0 wash). The pH 4.0 wash is optional in high stringency selection, but it cannot be completely combined with the 65° C. wash. For example, phage die in about pH 4.0 buffer at about 65° C.

High stringency selection may be enhanced by lowering the antibody density on the bead or other solid-phase support. In this case, lowering the probability that a given phage will bind more than one antibody molecule selects for higher affinity epitopes.

Lower stringency selection is performed instead by washing about 3 to about 20 times at neutral pH at about room temperature. A pH 4.0 wash may optionally follow.

Elution of high affinity epitopes is the next step (hereinafter the pH 2.0 elution) for both high and low stringency selection. Phage bound to solid-phase supported antibody are incubated briefly (about 1 to about 15 minutes) in a low pH buffer in about 0.1–10 mg/ml BSA or other non-specific binder. The buffer pH can vary from about 2.3 to about 1.0, with 2.2 being preferred. Temperature conditions range from about 4° C. to about 37° C., with about room temperature being desirable. Preferred buffered conditions are 0.1 N glycine•HCL, pH 2.2, 1 mg/ml BSA at about room temperature.

After the pH 2.0 elution, the eluted solution containing the phage is neutralized by standard and well-known techniques. The eluted phage are grown in infectable *E. coli*, e.g., tet$^+$ phage are grown in tet$^-$ *E. coli*, e.g., K91K cells, on media containing tetracycline.

This concludes one cycle of selection, either at high stringency or low stringency. Repetition of the cycle is often found advantageous, as it lowers the complexity of eluted phage to manageable quantities (less than about $10^5$). Repeating the cycle about 2–10 times, preferably 3–5 times, is found most practical. It will be apparent to those skilled in the art that indicated variations are readily performed and evaluated, such as switching from high stringency to low stringency on one or more cycles of selection, or changing the buffer or its pH.

B. Identification With Antibody Lifts

A second selection method which may be used in addition to the method described above is to identify, using antibody lifts, those clones with desired epitopes. The principle is to place an overlay in culture plates of cells infected with selected phage epitopes, remove the overlay, block the overlay, incubate the blocked overlay with desired antibody, label the bound antibody, and locate on the original culture plate those colonies that bind the antibody. Versions of this overlay technique that differ from the present method exist in the literature. Methods known are typically adopted for use with plaque formers, unlike the present invention. See, e.g., Young, R. A. et al., *Proc Natl. Acad Sci.*, 80, 1194 (1983); Ausubel, F. M. et al., (eds.), "Screening Recombinant DNA Libraries," in *Current Protocols in Molecular Biology*, Chapter 6, Greene 1989; and Davis, L. G. et al., *Basic Methods in Molecular Biology*, pp. 214–215, Elsevier 1986.

Plates having epitope phage-infected colonies are incubated until the colonies are sufficiently large, i.e., between about 1 mm and about 4 mm in diameter, yielding mature plates.

Mature plates are overlaid with a disk that binds proteins. The disc is typically nitrocellulose, but it may also be IMMOBILON P, cellulose acetate and the like. The disk is immediately removed and subjected to further treatment.

Blocking the overlay or disk is first performed to eliminate or substantially reduce the background of non-specific interactions. Useful blocking agents include BSA, milk solids and similar proteinaceous preparations. One preferred embodiment for this blocking step is soaking each disk for 4 hours in TABS, 10% evaporated milk, at room temperature. A preferred range is incubation for at least 2 hours, in a buffer near neutrality (about pH 5.0–8.0) containing about 0.1% (v/v) to about 1.0% (v/v) neutral detergent, in about 1% to about 20% blocking agent, within a temperature range of about 4° C. to about 80° C.

Washing the blocked disks to remove excess blocking agent follows, and is carried out in a buffer lacking the blocking agent. One preferred embodiment for this washing step is soaking each disk two or three times in TTBS, pH 7.3–7.5, at room temperature. A preferred range of conditions is soaking for at least 10 minutes, in a buffer with a pH that does not destroy antibody (5.0–8.0), containing 0.1% (v/v) to 1.0% (v/v) neutral detergent, within a temperature range of about 4° C. to about 80° C.

Contacting the disk with screening antibody follows. One preferred embodiment is incubating the washed disks overnight at 4° C. with gentle rocking, in TTBS, 1% evaporated milk, 0.5 to 1.0 µg/ml antibody. A preferred range of conditions is incubating the disks for at least 4 hours, within a temperature range of between about 4° C. and about 65° C., in buffer near neutrality containing about 0.1 % (v/v) to about 1.0% (v/v) neutral detergent, in 0.1% to 5% blocking agent, and 0.1 to 5 µg/µl antibody.

A second series of washes are performed, here to remove excess or unbound antibody. One preferred embodiment is soaking each disk four times in TTBS for 20 minutes at room temperature with gentle rocking. Preferred ranges of conditions are at least 2 soaks in buffer without blocking agents at a pH near neutrality (6.0–8.0), for 5 minutes to 1 hour, between about 10° C. and 45° C.

The resulting washed disks having bound antibody are treated with a labeled second-stage reagent to determine the location of the bound antibody and the corresponding epitope clone. Any labeled or tagged second-stage reagent useful for binding the bound antibody can in principle be incorporated into the procedure for the purposes of identifying the clones having epitopes bound by antibody. One preferred embodiment is soaking the washed disks having bound antibody in TTBS, 1% milk, $^{125}$I-protein A (0.5 to 1µ curie/ml) for 1.5 to 3 hours. Preferred ranges of conditions are incubating the disks for at least 1 hour, within a temperature range of between about 4° C. to about 65° C., in buffer near neutrality containing about 0.1% (v/v) to about 1.0% (v/v) neutral detergent, in about 0.1% to about 5% blocking agent and detectable quantities of labeled protein A. Another preferred second-stage reagent is labeled protein G, e.g., $^{125}$I-protein G. Other appropriate second-stage reagents include, but are not limited to, double antibody, such as $^{125}$I-labeled mouse anti-human IgG, or mouse anti-human IgG tagged with beta-galactosidase or peroxidase. Substantial purity of labeled second-stage reagent is desirable.

The disks having bound labeled antibody are now soaked or washed to remove unbound label. One preferred embodiment is soaking 20 minutes four times in TTBS. The location of the labeled, bound antibody on the disks is determined by conventional procedures appropriate for the labeled second-stage reagent. X-ray film is used for $^{125}$I. Chromogenic substrates are useful in a variety of enzyme-antibody detection kits.

Once the location of the bound antibody is determined, e.g., a pattern of dark spots on developed X-ray film, one identifies the appropriate colonies on the original mature plate, since the colonies are regrown as needed. Subsequent replating, growth, and sequencing gives a particular selected principal neutralizing epitope (SPNE).

Recombinant Fusion Polypeptides

For ease of evaluating SPNE as ligands, applicants have constructed recombinant shuttle vectors coding for RFPs of novel SPNE and selected peptides or fragments thereof, such as pIII (with or without a polyhistidine tail), Hep B core, Hep B surface-antigen or protein A. The methods for construction of fusion peptides are well known in the art. Coding sequences are prepared by ligation of other sequences, cloning, PCR, mutagenesis, organic synthesis, or combination thereof, in accordance with the principles and practice of constructing DNA sequences.

Once selection of desired phage epitopes in a phage epitope library has been made, it is necessary to determine the DNA sequences coding for a selected SPNE. The present invention utilizes PCR to amplify the SPNE and sequencing of the resulting fragment.

In particular, after one or more rounds of selection, *E. coli* colonies are grown overnight at about 37° C. in a suitable medium containing appropriate antibiotics. The supernatant is used as template in PCR reactions. The template is amplified using 100-fold excess of one primer over the other. Template and oligonucleotide primers (Primer 1008: 5'-TCG AAA GCA AGC TGA TAA ACC G-3' SEQ ID NO:1, located 106 nucleotides upstream of random insert and Primer 1009: 5'-ACA GAC AGC CCT CAT AGT TAG CG-3' SEQ ID NO:2, located 87 nucleotides downstream from random insert) are reacted in a volume of 100 µl containing KCl; Tris-HCl, about pH 8.3; $MgCl_2$; gelatin; each DNTP and a thermal-stable DNA polymerase, e.g., Taq and others appreciated by those of ordinary skill in the art. Mineral oil is placed over the reaction and amplification in a thermal cycler is carried out for an initial period at about 94° C. incubation, then about 30 cycles of about 30 seconds at about 94° C., about 1 minute at about 55° C. and about 2 minutes at about 72° C. followed by about 5 minute incubation at about 72° C. In a preferred embodiment, the mineral oil is removed, water added to the reactions, and the sample is centrifuged in a microconcetrator. The retentate volume is brought up to about 2 ml with water and centrifuged. The retentate is then collected by centrifugation. Retentate concentrations are determined by electrophoresis on an agarose gel containing Ethidium bromide and visualization under ultraviolet light. The retentate is dried along with enough limiting primer from PCR reaction (or internal primer 1059 5'-GTA AAT GAA TTT TCT GTA TGA GG-3' SEQ. ID NO:3, located, 27 nucleotides downstream from insert) to give about a 5:1 primer:template molar ratio. The DNA/primer mixture is resuspended in water and Tris•Buffer. The primer and template are annealed and chain termination sequencing reactions are set up and run. A sequencing gel is run on the PCR product. The gel is dried and exposed to X-ray film overnight and the sequence is then determined. Alternatively, other methods of sequencing the PCR product may be used, e.g., chemical cleavage, automated fluorescence sequencing described by Tracy, T E and L S Mulcahy, *Biotechniques*, 11, 68 (1991) or modifications thereof.

For the particular RFPs of this invention, DNA sequences coding for a selected SPNE are ligated in frame to DNA sequences coding for pIII, Hep B core or protein A. The resulting DNA fragment is expressed in any one of a wide variety of readily available systems, e.g., *E. coli* BL21 (DE3), as also discussed later.

SPNE-pIII-(His)$_6$ Fusions

The HIV/pIII fusion was expressed in *E. coli* using the T7 polymerase system from Rosenberg, A. H. et al., *Gene* 56, 125 (1987). The plasmid pET-3a (commercially available from Novagen, Madison, Wis.) was digested with Xba I and BamHI and the 5 kb vector fragment isolated. The isolated vector fragment was ligated with the Xba I, BgI II-digested HIV-pIII fusion prepared by polymerase chain reaction (PCR) of the candidate HIV fusion phage clones.

Two synthetic DNA oligomers were used to amplify a portion of the phage pIII gene (including the HIV sequence) and append sequences which permit efficient expression and purification of the pIII product. The first synthetic DNA oligomers, 5'-CCC TCT AGA AAT AAT TTT GTT TAA CTT TAA GAA GOA GAT ATA CAT ATG GCC GAC GGG GCT-3' (SEQ ID NO: 4), has homology with the fuse phage III gene with the sequences encoding the mature amino terminus of Ala-Asp-Gly-Ala (SEQ ID NO:5). PCR amplification from this site incorporates the sequences encoding the mature pIII protein and rebuilds the pET-3a vector from the Xba I sit to the initiating methionine.

The second synthetic DNA oligomer, sequence 5'-CTC AGA TCT ATT AAT GGT GAT GGT GAT GAT GTA TTT TGT CAC AAT CAA TAG AAA ATT C-3' (SEQ ID NO:6) encodes the reverse strand of the carboxyl-terminal portion of pIII ending with residues Cys-Asp-Lys-Ile (SEQ ID NO:7). PCR with this oligo rebuilds the fuse phage pIII gene up to the transmembrane domain and appends six histidine residues to the carboxyl-terminal isoleucine. The presence of the histidine residues facilitates purification of the pIII fusion protein by metal chelation chromatography (Hochuli, E. et al., *J. Chromat.* 411, 177 (1987) using nitrilotriacetic (NTA) resin (available from Qiagen, Chatsworth, Calif.).

Expression of the pIII fusion is obtained by transforming the expression plasmid into *E. coli* strain BL21 (DE3) (Rosenberg, A. H. et al., supra; U.S. Pat. No. 4,952,496; Steen, et al., *EMBO J.* %, 1099 (1986). This strain contains the T7 phage RNA polymerase gene under control of the lac operator/promoter. Addition of isopropylthio-galactoside (IPTG) at culture OD$_{600}$=0.6–0.8 induces T17 RNA polymerase expression which transcribes pIII mRNA to high levels. This RNA is translated yielding pIII fusion protein which is harvested 3–4 hours post induction and chromatographed on NTA resin.

In the alternative, the fusion peptides can be made by synthetic organic means, although this method is limited by feasibility and by practicality to smaller fusion peptides. See also the section on organic synthesis of SPNE, above.

Selecting Ligands for a Given Target Molecule

Selection of the ligand-target molecule system is critical for any affinity chromatography purification scheme. Knowledge of the kinetics of the ligand and target molecule interaction is important for rationally designing the steps, materials and solutions used in the purification of a given target molecule. Knowledge of the affinity constant ($K_a$) alone may not be adequate for optimal system selection. In particular, knowledge of the association constant ($k_a$) and the dissociation constant ($k_d$) is required to optimally design a given purification scheme. For immunoaffinity chromatography, this knowledge has been, until recently, elusive because of the difficulty in studying antibody—antigen interactions. Several methods have been described to identify antigens that bind to a specific antibody. Such methods include, but are not limited to, agglutination reactions, precipitation reactions, immunoassays, immunofluorescence, fluorescence-activated cell sorting. These methods do not represent the primary interaction between antibodies and a given epitope, but, rather, depend on secondary interactions for detection. This, therefore, makes it impossible to determine exactly the $k_a$ and $k_d$ for a given antibody—antigen interaction and ultimately renders an optimally designed purification scheme a misnomer.

Recently, however, quantitative analysis of molecular interactions in real time has been described (Karlsson, R., Michaelsson, A. and Mattsson, L. (1991). Kinetic analysis of monoclonal antibody-antigen interactions is possible with a new biosensor based analytical system. *Journal of Immunological Methods*, 145:229–240). This analysis relies upon surface plasmon resonance as a direct optical sensing technique, based on total internal reflectance, to study molecular interactions, e.g., antibody—antigen, in real time.

In a real-time biospecific interaction, light is coupled resonantly into electric oscillations, or surface plasmons, at a metal surface, e.g., gold. Such oscillations give rise to a nonpropagating evanescent wave that extends from the metal surface into the sample solution, decaying exponentially as a function of distance. Macromolecular complexes formed at the metal-liquid interface, resulting in a change in refractive index of the liquid media at the interface, perturb the evanescent wave and alter the propagation characteristics of the plasoms. Changes in the propagation characteristics of the plasmons in turn alter the characteristics of the internally reflected light. Such changes are ultimately detected and quantitated by means of a diode array. This instrument uses a layer of gold modified with carboxylated dextran to provide a hydrophilic surface for immobilization of macromolecules, e.g., proteins, immunoglobulins and antibodies. It is possible to site-direct the immobilization chemistry for macromolecule immobilization. For example, activation of the dextran matrix using a mixture of N-ethyl-N'-(3-diethylaminopropyl)carbodiimide (EDC) and N-Hydroxy-succinimide (NHS) produces NHS-esters on the matrix for reaction with primary amino-containing macromolecules. Other methods use hydrazine, to produce an active hydrazine matrix, and sulfo-m-maleimidobenzoyl-N-hydroxysulfosuccinrimde ester (sulfo-MBS), to produce an active sulhydryl matrix. After one of the reactants is covalently attached to the dextran matrix, the other is introduced in a flow passing over the surface. The resonance angle depends on the refractive index in the vicinity of the metal surface and is monitored continuously, thus allowing the association or dissociation of molecules from the sensor surface to be followed in real time. No labeling of the ligand or the target molecules is required.

In one embodiment of this invention, 447 antibody is covalently bound to the dextran matrix after less than five minutes of activation. Specifically, activation is accomplished using a continuous flow of HBS (10 mM HEPES, 0.15 M NaCl, 3.4 mM EDTA and 0.05% Surfactant P20), about pH 7.4, passing over the sensor surface. The carboxylated dextran matrix is then activated by injecting a solution containing EDC and NHS. The target molecule is then injected followed by a blocking agent such as ethanolamine to block remaining NHS-ester groups. The target molecule-dextran matrix is then conditioned with an acid, e.g., HCl. After this step, the sensor surface is ready for use. An immobilization level of about 10,000 to about 15,000 RU, with about 10,000 RU being preferred, corresponding to 10–15 ng/mm$^2$ of 447 antibody is preferred.

The 447 antibody is used to capture antigenic RFPs. An analytical cycle consists of injecting a fusion peptide in supernatant from about 1.5 minutes to about 5 minutes, preferably for about 3 minutes, dissociation of the fusion protein in buffer flow and regeneration of the surface with 100 mM HCl for 3 minutes. Analytical cycles can be programmed and the entire analysis is completely automated.

Cell Culture

The medium used in this invention may be, but is not limited to, HEPES, MEM, NCTC, IMDM and RPMI media. Any cell line that is capable of expressing antibody, receptors or any other target molecule of interest is included within this invention. Cells lines include but are not limited to, NS/O. The medium may be conditioned from about 1 to about 14 days, with 8 days being preferred. Cells and cell debris may be removed from the medium using centrifugation, filtration or other methods known in the art.

In a preferred embodiment of this invention, a NS/O cell construct is grown in IMDM medium supplemented with protein growth factors for 8 days. The antibody containing conditioned medium is filtered by passing the conditioned medium through a 0.1 μm filtration device followed by passing the resulting medium through a 0.22 μm sterile filtration device to remove the intact cells and cell debris.

Affinity Chromatography

Affinity chromatography provides a convenient method for preparing pure macromolecules. In particular, immunoaffinity chromatography takes advantage of the high affinity interaction between an antigenic peptide or polypeptide and its corresponding antibody. Purified antibody may be obtained using immunoaffinity chromatography wherein the antigenic peptide or polypeptide is coupled to an inert matrix and is used as a selective adsorbent for antibody isolation.

Inmunoaffinity chromatography comprises three principle steps; adsorption, washing and elution. Adsorption and elution are the most critical for success. Adsorption is the step wherein the target molecule is bound to the ligand. Adsorption is accomplished by contacting the sample containing the target molecule with the ligand bound to solid support matrix in a suitable medium within a column. Washing is the step wherein impurities present in the fluid volume of the column as well as those bound nonspecifically to the ligand are removed. Washing is accomplished by passing a volume of physiological buffer, such as phosphate buffered saline, about pH 7.2, through the column. The volume of buffer used in the washing step should not be so great as to result in target molecule loss but, on the other hand, not so limited so as not to remove impurities. Elution is the step wherein the target molecule is removed from the column by using a solvent that reduces the affinity of the target molecule to the ligand or the affinity of the ligand-target molecule complex to the solid support. Elution of an antibody coupled to the antigen may be accomplished by either a salt gradient, to change the pH; buffered step-gradient, to change the ionic strength; or other methods.

Proper selection of a solid support for the ligand is critical for specific adsorption. The ideal matrix should possess several characteristics including, macroporosity, mechanical stability, ease of activation, hydrophilicity, and inertness, i.e., low nonspecific adsorption. No matrix is ideal in all of these respects; the matrix is often determined empirically. Matrices commonly used by those skilled in the art include cross-linked dextran, agarose, polyacrylamide, cellulose, silica and poly(hydroxyethylmethacrylate). For immunoadsorbents, beaded agarose is the preferred solid support by those skilled in the art due to its high adsorptive capacity for proteins, high porosity, hydrophilicity, chemical stability, lack of charge and relative inertness toward nonspecific adsorption.

Ligands may be physically adsorbed to matrices or covalently attached to polymeric matrices containing hydroxylic or amino groups by means of bifunctional reagents. Attachment usually requires two steps, activation of the matrix and coupling of the ligand to the activated matrix. Activated matrices are available commercially. The selection method for coupling the ligand to the matrix is dictated in part by the choice of matrix, and, in part, by the choice of ligand.

Most methods commonly used to immobilize peptide or polypeptide ligands are based on coupling of amino groups. The polypeptide ligand must be coupled in a manner that will not interfere with its ability to be recognized by the target molecule. Methods for activation and coupling, commonly used by those skilled in the art, include but are not limited to cyanogen bromide, bisoxirane, N-hydroxysuccinimide esters and divinlysulfone. For detailed procedures see, e.g., Axen et al., *Nature* (London) 214, 1302 (1967), Porath et al., *Protides Biol. Fluids, Proc. Colloq.* 18:401 (1970), and Porath et al., *Nature* (London) 238, 261 (1972). The preferred method for activating agarose matrices by those skilled in the art is with cyanogen bromide. This method is relatively simple and can be performed entirely in aqueous solutions.

For successful use of affinity chromatography, the polymer-bound ligand must be sufficiently distant from the polymer surface to minimize steric interference. This is accomplished by inserting an interconnecting link or spacer between the ligand and the matrix. There are two methods commonly employed for introducing spacers. First, the ligand may be prepared with a long hydrocarbon chain containing an amino group which will serve as the spacer. Second, the spacer may be bound directly to the matrix so that the ligand can be attached directly to these spacers. Types of spacers commonly used by those skilled in the art include but are not limited to cystamine, p-aminobenzoic acid, tyramine and p-hydroxy-mercuribenzoate.

The specific buffering conditions used for equilibrating the affinity column in preparation for sample application should reflect the specific properties of the interacting system being used. The nature of the buffer used, including its pH and ionic strength, should be optimal for the ligand-target molecule system. The target molecule sample applied to the column should be contained in the same buffer used to equilibrate the column. After sample application and adsorption, the column should be washed with the starting buffer to remove any unbound sample and any impurities. It is also common to then wash the column with buffers different from the starting buffer in order to remove non-specifically adsorbed substances.

Elution of the target molecule may be accomplished by a number of methods, including but not limited to these presented here. There are no covalent bonds involved in the interaction between antibody and antigen. Thus, the conditions of the buffer may be changed such that the affinity of the antigen-antibody complex falls sufficiently to destroy effective binding to each other or to the solid support. This is achieved by altering the pH, or the ionic strength of the buffer or both, or by chaotropic ions, e.g., cyanates. Increased separation may be obtained by gradient elution. In the case of immunosorption, the binding of a polypeptide antigen and antibody complex may be so strong that more harsh elution conditions are necessary, such as the use of buffers which are very strongly acidic or basic. Such elution conditions may irreversibly denature the desired antibody or exacerbate antigen leakage. Other methods of elution include use of chaotropic agents such as KSCN; organic solvents, e.g., ethylene glycol, DMSO, or acetonitrile; denaturing agents, e.g., 8 M urea or 6 M guanine; electrophoretic elution; pressure induced elution and metal ion elution. Incomplete elution results in both loss of product and loss of column capacity. Ideally, the elution conditions should allow for complete elution of the product after one or two column volumes have passed through the column. The exact nature of the elution agent is dictated by the nature of the antigen-antibody interaction. Detailed discussions of affinity chromatography can be found in *Affinity Chromatography: A Practical Approach*, edited by Dean P. D. G., Johnson, W. S., Middle, F. A., *Affinity Chromatography, Principles and Methods*, as published by Pharmacia, (Pharmacia LKB Biotechnology, Uppsala, Sweden), and *Immunoaffinity Purification: Basic Principles and Operational Considerations*, Yarmush, M. L, et al., (1992) *Biotech Adv.*, 10:412–446.

In one embodiment of the present invention, a column of a quadradridentate chelating adsorbant, Ni++-nitrilotriacetate-SEPHAROSE, is prepared and charged with the RFP containing a hexahistidine tail (SEQ ID NO:8). The column is equilibrated with a phosphate buffer, about pH 7.0, containing NaCl. Conditioned medium containing HIV-1 antibody is loaded on the column and is washed with about 5 column volumes of the same buffer. The RFP-bound antibody is washed with TWEEN 80 is sodium phosphate buffer, about pH 7.0, containing sodium chloride. The wash step is performed by passing about 2 column volumes of the buffer-TWEEN-sodium chloride solution followed by a stopped flow incubation and subsequent column washes. The antibody is eluted from the RFP with a gradient of NaCl. Alternatively, the antibody is eluted from the RFP with gradient of $MgCl_2$.

Another embodiment of the present invention uses a modification of the method of Porath (Porath, J., *Methods in Enzymology*, 34, 13 (1974)) wherein a volume of CNBr-activated SEPHAROSE is incubated with the RFP containing a lysine cluster tail (Gly-Ala-Lys-Lys-Ala-Lys, SEQ ID NO:9) for about 8 to 16 hours at about 0° C. to about 10° C., preferably about 4° C., in sodium borate buffer, about pH 8.5. A column of the coupled SEPHAROSE is prepared and equilibrated with phosphate buffer, about pH 7.0, containing NaCl. Conditioned medium containing HIV-1 antibody is loaded on the column and is washed with the same buffer. The RFP-bound antibody is washed with TWEEN 80 in sodium phosphate buffer, about pH 7.0, containing sodium chloride. The wash step is performed by passing at least one column volume of the buffer-TWEEN-sodium chloride solution followed by a stopped flow incubation and subsequent column washes. An additional wash step is performed in the same column with $MgCl_2$ followed by at least one wash with sodium phosphate buffer, about pH 7.0. The antibody is step-eluted from the RFP using glycine, about pH 3.0, and neutralized to about pH 7.0 with Tris-HCl, about pH 8.0. Alternatively, the antibody may be step-eluted from the RFP using $MgCl_2$ in acetic acid and neutralized to about pH 7.0 using Tris-HCl, about pH 8.0.

Yet another embodiment of the present invention uses a volume of SEPHAROSE activated with 2-Fluoro-1-methylpyridinium toluene-4-sulfonate (FMP) coupled with the RFP (sequence presented above) according to published methods (Ngo, T. T., *Biotechnology*, 4; 134 (1986). A column of the coupled SEPHAROSE is prepared and equilibrated with phosphate buffer, about pH 7.0, containing NaCl. Conditioned medium containing HIV-1 antibody is loaded on the column and is washed with at least one column volume of the same buffer. The RFP-bound antibody is washed with TWEEN 80 in sodium phosphate buffer, about pH 7.0, containing NaCl. The wash step is performed by passing volumes of the buffer-TWEEN-sodium chloride solution through the column followed by a stopped flow incubation and a subsequent column wash. A second wash step is performed in the same column with $MgCl_2$ followed by a wash with sodium phosphate buffer, about pH 7.0. The product is step-eluted using $MgCl_2$ in acetic acid and neutralized to about pH 7.0 using Tris-HCl, about pH 8.0.

While the foregoing specification teaches the principles of the present invention, with examples provided for the purposes of illustration, it will be understood that the practice of the invention encompasses all of the usual variations, adaptations, modifications, deletions or additions of procedures and protocols described herein, as come within the scope of the following claims and its equivalents.

Specifically, 447 antibody described here is useful as a broadly neutralizing monoclonal antibody against HIV. This "447 antibody" binds to about 90% of all known HIV serotypes and neutralizes HIV. It was isolated from a human patient.

Other receptors such as cytokines, other antibodies, protein receptors, recombinant antigen mimics and other conformational epitope mimics can be prepared according to the processes of the present invention and are included within the scope thereof.

The following examples are illustrative of the practice of the invention without being limited in any way.

EXAMPLE 1

Library Construction

A. Random Library

A phage library containing random fifteen amino acid epitopes was constructed by the methods of Scott, J. K., et al., *Science*, 249, 386 (1990). In this protocol, synthetic 110 BP BglI fragments were prepared containing degenerate coding sequence $(NNK)_{15}$, wherein N stands for an equal mixture of G, A, T and C, and K stands for an equal mixture of G and T. The library was constructed by ligating the synthetic 110 bp BglI fragments in phage fUSE5 and transfecting *E. coli* cells with the ligation product by electroporation. The resulting phage oligopeptide epitope library (also known as Library ALPHA) had a complexity of approximately $40 \times 10^6$ different epitopes.

EXAMPLE 2

Bead Coating Procedure

Polystyrene beads (d=0.25 inch) were coated with between 1 and 10 μg of 447 antibody per ml in 50 mM $Na_2CO_3$, pH 9.67, 0.02% sodium azide. (Note that any solid phase adsorbent should work). Beads were incubated in the antibody solution at 4° C. overnight.

The next day the coated beads were washed 3× with phosphate buffered saline and 1× with water. After washing, the antibody-coated beads were air dried and stored frozen at −20° C. until needed. Before use, the antibody-coated beads were coated with 10 mg/ml BSA (to block free sites on the plastic) in TTBS (50 mM Tris, pH 7.5, 150 mM NaCl, 0.5% (v/v) TWEEN 20) for four or more hours. Each batch of beads was checked for antibody activity by its ability to bind $^{125}I$ protein A, before being used in a phage selection screen.

EXAMPLE 3

Stringent Phage Selection with Antibody-Coated Beads

A. First Method—Low Stringency

The random epitope phage library ALPHA was incubated at 4° C. overnight with gentle rocking, with antibody-coated beads in TTBS, 1 mg/ml BSA. Typically, a total volume of 1 cc containing $10^{11}$ phage was used. The next day the bead, containing the bound phage, was washed ten to twelve times in TTBS, in a volume of 10 cc per wash, at room temperature, with a gentle rocking motion, for ten minutes per wash. The liquid was carefully drained of the bead between each wash. After the last wash, the bound phage were eluted off the bead by incubating for 5 minutes at room temperature in a minimal volume (typically 200 μl) of 0.1 N HCl, adjusted to pH 2.2 with glycine, 1 mg/ml BSA. The solution with the eluted phage was neutralized by adding 12 μl of 2 M Tris, pH unadjusted, per 200 μl phage solution. The eluted phage were then used to infect *E. coli* K91K cells. Infected cells were plated onto LB agar plates containing 40 μg/ml tetracycline. Since the phage carry a tetracycline resistance marker, only infected cells grow on the plates. Typically, one bead selected between 5000 and 100,000 independent phage. Phage were harvested and precipitated twice with PEG (polyethylene glycol). The precipitated phage were then titered and approximately $10^{10}$ of the first round selected phage were again incubated with a 447-antibody coated bead, washed as described above, regrown and harvested. Three cycles of selection and growth were performed. *E. coli* infected with phage were plated as clonal isolates.

B. Second Method—High Stringency

The random epitope library was incubated at 4° C. overnight with gentle rocking, with antibody-coated beads in TTBS, 1 mg/ml BSA. Typically a total volume of 1 cc containing on the order of $10^{11}$ phage was used, corresponding to the complexity of the library×1000. The next day, the bead containing the bound phage was washed ten times in TTBS, in a volume of 10 cc per wash, at 65° C., with gentle rocking, for 10 minutes per wash. Note that 65° C. in TTBS does not destroy phage. There followed one wash at room temperature in TTBS, pH 4.0. The liquid was carefully drained off the bead between each wash. Next, the bound phage were eluted off the bead by incubating for five minutes at room temperature in 200 μl of 0.1 N HCl, adjusted to pH 2.2 with glycine, 1 mg/ml BSA. The phage solution was neutralized by adding 12 μl of 2 M Tris, pH unadjusted. The eluted phage were then used to infect *E. coli* K91K cells. Infected cells were grown in 1× Luria broth containing 40 μg/ml tetracycline (250 cc) and incubated with shaking for 48 hours at 37° C. Phage were harvested and precipitated twice with PEG (polyethylene glycol). The precipitated phage were then titered and approximately $10^{10}$ of the first round selected phage were again incubated with a 447-antibody coated bead, washed as described above, regrown and harvested. Three cycles of selection and growth were performed. *E. coli* infected with phage were plated as clonal isolates.

EXAMPLE 4

PCR Sequencing

After one or more rounds of selection according to Example 3, the infected *E. coli* colonies were grown overnight at 37° C. in 1× Luria broth, 40 μg/ml tetracycline on a rollerdrum. The cells were pelleted and 1.0 μl of supernatant was used as template in PCR reactions. The template was amplified using 100-fold excess of one primer over the other. Template and oligonucleotide primers (Primer 1008: 5'-TCG AAA GCA AGC TGA TAA ACC G-3' SEQ ID NO:1, located $10^6$ nucleotides upstream of random insert and Primer 1009: 5'-ACA GAC AGC CCT CAT AGT TAG CG-3' SEQ ID NO:2, located 87 nucleotides downstream from random insert) were reacted in a volume of 100 μl containing 50 mM KCl; 10 mM Tris-HCl, pH 8.3; 1.5 mM $MgCl_2$; 0.01% (w/v) gelatin, 200 μM each dNTP and 2.5 units Taq polymerase. Reactions were overlaid with mineral oil and amplified in a thermal cycler for an initial 8 minute 94° C. incubation, then 30 cycles of 30 seconds at 94° C., 1 minute at 55° C. and 2 minutes at 72° C. followed by a 5 minute incubation at 72° C. The mineral oil was removed, 2 ml of water added to the reactions, and the sample centrifuged in a microconcentrator for 30 minutes at 1000×g. The retentate volume was brought up to 2 ml with water and centrifuged as above. The retentate was the collected by centrifugation for 2 minutes at 500×g. Retentate concentrations were determined by electrophoresis on a 1% agarose gel containing 0.5 μg/ml Ethidium bromide and visualization under ultraviolet light. The retentate was dried along with enough limiting primer from PCR reaction (or internal primer 1059 5'-GTA AAT GAA TTT TCT GTA TGA GG-3' SEQ. ID NO:3, located 27 nucleotides downstream from insert) to give 5:1 primer:template molar ratio. The DNA/primer mixture was resuspended in 8 μl water and 2 μl Tris•Buffer (200 mM Tris HCl. pH 7.5; 100 mM $MgCl_2$; 250 mM NaCl) Kit). The primer and template were annealed and chain termination sequencing reactions were set up. A 6% sequencing gel was run at 60 watts for approximately 1 hour and 30 minutes. The gel was dried and exposed to X-ray film overnight and the sequence was determined.

EXAMPLE 5

SPNE-pIII-(His)$_6$ Fusions

The HIV/pIII fusion was expressed in *E. coli* using the T7 polymerase system from Rosenberg, A. H. et al., *Gene* 56, 125 (1987). The plasmid pET-3a (commercially available from Novagen, Madison, Wis.) was digested with Xba I and BamHI and the 5 kb vector fragment isolated. The isolated vector fragment was ligated with the Xba I, BgI II-digested HIV-pIII fusion prepared by polymerase chain reaction (PCR) of the candidate HIV fusion phage clones.

Two synthetic DNA oligomers were used to amplify a portion of the phage pIII gene (including the HIV sequence) and append sequences which permit efficient expression and purification of the pIII product. The first synthetic DNA oligomer, 5'-CCC TCT AGA AAT AAT TTT GTT TAA CTT TAA GAA GGA GAT ATA CAT ATG GCC GAC GGG GCT-3' (SEQ ID NO: 4), has homology with the fuse phage im gene with the sequences encoding the mature amino terminus of Ala-Asp-Gly-Ala (SEQ ID NO:5). PCR amplification from this site incorporates the sequences encoding the mature pIII protein and rebuilds the pET-3a vector from the Xba I sit to the initiating methionine.

The second synthetic DNA oligomer, sequence 5'-CTC AGA TCT ATT AAT GGT GAT GOT GAT GAT GTA TTT TGT CAC AAT CAA TAG AAA ATT C-3' (SEQ ID NO:6) encodes the reverse strand of the carboxyl-terminal portion of pIII ending with residues Cys-Asp-Lys-Ile (SEQ ID NO:7). PCR with this oligo rebuilds the fuse phage pIII gene up to the transmembrane domain and appends six histidine residues to the carboxyl-terminal isoleucine. The presence of the histidine residues facilitates purification of the pIII fusion protein by metal chelation chromatography (Hochuli, E. et al., *J. Chromat.*, 411, 177 (1987) using nitrilotriacetic (NTA) resin (available from Qiagen, Chatsworth, Calif.).

Expression of the pIII fusion is obtained by transforming the expression plasmid into *E. coli* strain BL21 (DE3) (Rosenberg, A. H. et al., supra; U.S. Pat. No. 4,952,496; Steen, et al., *EMBO J.* %, 1099 (1986). This strain contains the T7 phage RNA polymerase gene under control of the lac operator/promoter. Addition of isopropylthio-galactoside (IPTG) at culture $OD_{600}$=0.6–0.8 induces T7 RNA polymerase expression which transcribes pIII mRNA to high levels. This RNA is translated yielding pIII fusion protein which is harvested 3–4 hours post induction and chromatographed on NTA resin.

EXAMPLE 6

Identification of Peptide-phage Fusion Protein for Use in Antibody Purification

A quantity of 447 antibody was covalently bound to a hydrophillic carboxymethlyated dextran modified gold surface by N-hydroxysuccinimide/carbodiimide mediated amine coupling following the manufacturer's recommendations, however, the time of activation was reduced to 4 minutes. Specifically, a continuous flow of HBS (10 mM HEPES, 0.15 M NaCl, 3.4 mM EDTA and 0.05% Surfactant P20), pH 7.4, passed over the sensor surface at 5 $\mu$l/min. The carboxylated dextran matrix was activated by the injection of 20 $\mu$l of a solution containing 0.2 M EDC and 0.05 M NHS. Next, 20 $\mu$L of 447 antibody (25 $\mu$g/mL in 10 mM acetate buffer, pH 4.75) were injected followed by 35 $\mu$l of ethanolamine to block remaining NHS-ester groups. After conditioning with 15 $\mu$l of 100 mM HCl, the sensor surface was ready for use. The immobilization level was X,000–X,000 RU, corresponding to X-Y ng/mm$^2$ of 447 antibody.

The 447 antibody was used to capture fusion peptides. An analytical cycle consisted of injecting the fusion peptide in supernatant for 3 minutes, dissociation of the fusion protein in buffer flow and regeneration of the surface with 100 mM HCl for 3 minutes. For the determination of the rate and affinity constants a flow rate of 3 $\mu$l/min and 36 $\mu$l of fusion peptide solution was used. In some cases where only the association rate constant was determined, a flow rate of 10 $\mu$l/min and 30 $\mu$l of fusion peptide was employed. Analytical cycles were programmed and the entire analysis was completely automated.

The following fusion peptides were tested: 447-22 (SEQ ID NO:10), 692-A12 (SEQ ID NO:11), 692-B12 (SEQ ID NO:12), 692-C12 (SEQ ID NO:13), 692-D12 (SEQ ID NO:14), 792-A13 (SEQ ID NO:15), 792-B13 (SEQ ID NO:16),792-C13 (SEQ ID NO:17). gp120(IIIB) (Meyers, et al., *Human Retroviruses in AIDS: A Compilation and Analysis of Amino Acids and Nucleic Acid Sequences*, (1993) Los Alamos National Laboratory, Los Alamos, N.Mex., USA) and protein A (Uhles, M., et al., (1984) *J. Bio. Chem.*, 250, 1695–1702) were also tested for comparative purposes.

Results:

TABLE 1

| Binding protein | k assoc   | k diss              |
| --------------- | --------- | ------------------- |
| 447-22          | 0         | 0                   |
| 692-A12         | na        | na                  |
| 692-B12         | 6.81E +04 | 2.440E-03           |
| 692-C12         | 4.73E+04  | 5.10E-04            |
|                 |           | 7.10E-04            |
| 692-D12         | na        | na                  |
| 792-A13         | 2.52E+04  | 1.77E-03            |
|                 |           | 2.74B-03            |
| 792-B13         | 3.62E+04  | 1.18E-03            |
|                 |           | 1.26E-03            |
| 792-C13         | 3.46E+04  | 1.30E-03            |
|                 |           | 1.95E-03            |
| gp120 (IIIB)    | 3.6E+05   | 3.44E-04            |
|                 |           | 3.90E-04            |
| protein A       | 6.30E+04  | 1.30E-04            |
|                 |           | 1.6E-04             |

EXAMPLE 7

Process for Selecting and Purifying Desired Antibody Receptor-Method I

Cell Culture

Antibody containing conditioned medium is obtained from suspension cultures of NS/O cell construct grown in IMDM medium supplemented with protein growth factors for 8 days. The intact cells and cell debris are removed by 0.1 $\mu$m filtration followed by 0.22 $\mu$m sterile filtration.

Purification

A 20.0 mL column of a quadradridentate chelating adsorbant, Ni++-nitrilotriacetate-SEPHAROSE is prepared and charged with 100 to 200 mg of the RFP containing a hexahistidine tail (sequence presented above). The column is equilibrated with 10 mM phosphate buffer, pH 7.0, containing 100 mM NaCl. Approximately 2 L of conditioned medium containing 447 antibody is loaded on the column and is washed with 5 column volumes of the same buffer. The RFP-bound antibody is washed with 0.05% (v/v) TWEEN 80 in 10 mM sodium phosphate buffer, pH 7.0, containing 120 mM sodium chloride. The wash step is performed by passing 2 column volumes of the buffer-TWEEN-sodium chloride solution followed by a stopped flow incubation of 30 minutes and a subsequent 2 column volume wash. The antibody is eluted from the RFP with a gradient of 0–1.0 M sodium chloride.

EXAMPLE 8

Process for Selecting and Purifying Desired Antibody receptor-Method II

Cell Culture

Antibody containing conditioned medium is obtained from suspension cultures of NS/O construct grown in IMDM medium supplemented with protein growth factors for 8 days. The intact cells and cells debris are removed by 0.1 µm filtration followed by 0.22 µm sterile filtration.

Purification

A 20 mL column of a quadradridentate chelating adsorbant, $Ni^{++}$-nitrilotriacetate-Sepharose is prepared and charged with 100–200 mg of the RFP containing a hexahistidine tail (SEQ ID NO:8). The column is equilibrated with 10 mM phosphate buffer, pH 7.0, containing 120 mM sodium chloride. Approximately 2 L of conditioned medium containing 447 antibody is loaded on the column and is washed with 5 column volumes of the same buffer. The RFP-bound antibody is washed with 0.05% (v/v) TWEEN 80 in 10 mM sodium phosphate buffer, pH 7.0., containing 120 mM sodium chloride. The wash step is performed by passing 2 column volumes of the buffer-TWEEN-sodium chloride solution followed by a stopped flow incubation of 30 minutes and a subsequent 2 column volume wash. The antibody is eluted from the RFP with a gradient of 0–1.0 M MgCl.

EXAMPLE 9

Process for Selecting and Purifying Desired Antibody Receptor-Method III

Cell Culture

Antibody containing conditioned medium is obtained from suspension cultures of NS/O construct grown in IMDM medium supplemented with protein growth factors for 8 days. The intact cells and cells debris are removed by 0.1 µm filtration followed by 0.22 µm sterile filtration.

Purification

Using a modification of the method of Porath (Porath, J., *Methods in Enzymology* 34, 13 (1974)), 20–25 ml of CNBr-activated Sepharose is incubated with 100 to 200 mg of the RFP containing a tail with lysine cluster ((SEQ ID NO:9)) for 8 to 16 hours at 4° C. in 100 mM sodium borate buffer, pH 8.5. A 20 ml column of the coupled Sepharose is prepared and equilibrated with 10 mM phosphate buffer, pH 7.0, containing 120 mM sodium chloride. Approximately 2 L of conditioned medium containing 447 antibody is loaded on the column and is washed with 5 column volumes of the same buffer. The RFP-bound antibody is washed with 0.05% (v/v) TWEEN 80 in 10 mM sodium phosphate buffer, pH 7.0., containing 120 mM sodium chloride. The wash step is performed by passing 2 column volumes of the buffer-TWEEN-sodium chloride solution followed by a stopped flow incubation of 30 minutes and a subsequent 2 column volume wash. A second wash step is performed in the same with 0.5 M $MgCl_2$ followed by a wash with 10 mM sodium phosphate buffer, pH 7.0. The product is step-eluted using 0.1 M glycine, pH 3.0, and neutralized to pH 7.0 with 1.0 M Tris-HCl, pH 8.0.

EXAMPLE 10

Process for Selecting and Purifying Desired Antibody Receptor-Method IV

Cell Culture

Antibody containing conditioned medium is obtained from suspension cultures of NS/O construct grown in IMDM medium supplemented with protein growth factors for 8 days. The intact cells and cells debris are removed by 0.1 µm filtration followed by 0.22 µm sterile filtration.

Purification

A volume of 20–25 mL of CNBr-activated Sepharose is incubated with 100–200 mg of the RFP containing a tail with lysine cluster (SEQ ID NO:9) for 8–16 hours at 4° C. in 100 mM sodium borate buffer, pH 8.5. A 20 ml column of the coupled Sepharose is prepared and equilibrated with 10 mM phosphate buffer, pH 7.0, containing 120 mM sodium chloride. Approximately 2 L of conditioned medium containing HIV-1 antibody is loaded on the column and is washed with 5 column volumes of the same buffer. The RFP-bound antibody is washed with 0.05% (v/v) TWEEN 80 in 10 mM sodium phosphate buffer, pH 7.0., containing 120 mM sodium chloride. The wash step is performed by passing 2 column volumes of the buffer-TWEEN-sodium chloride solution followed by a stopped flow incubation of 30 minutes and a subsequent 2 column volume wash. A second wash step is performed in the same with 0.5 M $MgCl_2$ followed by a wash with 10 mM sodium phosphate buffer, pH 7.0. The product is step-eluted using 0.30 M $MgCl_2$ in 2% Acetic Acid and neutralized to pH 7.0 using 1 M Tris-HCl, pH 8.0.

EXAMPLE 11

Process for Selecting and Purifying Desired Antibody Receptor-Method V

Cell Culture

Antibody containing conditioned medium is obtained from suspension cultures of NS/O construct grown in IMDM medium supplemented with protein growth factors for 8 days. The intact cells and cells debris are removed by 0.1 µm filtration followed by 0.22 µm sterile filtration.

Purification

A volume of 20–25 mL of Sepharose activated with 2-15-Fluoro-1-methylpyridinium toluene-4-sulfonate (FMP) is coupled with the RFP according to published methods (Ngo, T. T., *Biotechnology*, 4; 134 (1986)). A 20 ml column of the coupled Sepharose is prepared and equilibrated with 10 mM phosphate buffer, pH 7.0, containing 120 mM sodium chloride. Approximately 2 L of conditioned medium containing HIV-1 antibody is loaded on the column and is washed with 5 column volumes of the same buffer. The RFP-bound antibody is washed with 0.05% (v/v) TWEEN 80 in 10 mM sodium phosphate buffer, pH 7.0., containing 120 mM sodium chloride. The wash step is performed by passing 2 column volumes of the buffer-TWEEN-sodium chloride solution followed by a stopped flow incubation of 30 minutes and a subsequent 2 column volume wash. A second wash step is performed in the same with 0.5 M $MgCL_2$ followed by a wash with 10 mM sodium phosphate buffer, pH 7.0. The product is step-eluted using 0.30 M $MgCl_2$ in 2% Acetic Acid and neutralized to pH 7.0 using 1 M Tris-HCl, pH 8.0.

While the foregoing specification teaches the principles of the present invention, with examples provided for the purposes of illustration, it will be understood that the practice of the invention encompasses all of the usual variations, adaptations, modifications, deletions or additions of procedures and protocols described herein, as come within the scope of the following claims and its equivalents.

What is claimed is:

1. A method of purifying macromolecules which specifically bind to a ligand, wherein the macromolecules are present in an impure solution comprising:
    (a) preparing a phage library expressing a plurality of oligonucleotides comprising selected principle neutralization epitope (SPNE) candidate oligonucleotides;
    (b) screening the phage library to determine which candidate oligonucleotide is a SPNE of the macromolecules;
    (c) selecting a SPNE to be used as a ligand, wherein said ligand has an association constant within the range of about $1 \times 10^4$ to about $1 \times 10^6$ and a dissociation constant within the range of about $1 \times 10^{-2}$ to about $1 \times 10^{-5}$ with the macromolecules;
    (d) replicating the ligand to produce ligands;
    (e) binding the ligands to a support matrix to produce bound ligands;
    (f) introducing the bound ligands into a chromatography column;
    (g) contacting the impure solution containing the macromolecules with the bound ligands;
    (h) washing impurities from the column; and
    (i) eluting the purified macromolecules.

2. A method according to claim 1 wherein the macromolecules are antibodies.

3. A method according to claim 2 wherein the phage library has a complexity of approximately $40 \times 10^6$ different epitopes.

4. A method according to claim 2 wherein step b) comprises attaching an essentially pure preparation of antibody to a solid-phase support and incubating the solid-phase supported antibody with the phage library to effect binding of SPNE to the solid-phase supported antibody.

5. A method according to claim 2 wherein step c) comprises determining association constants and dissociation constants of SPNE-antibody interactions using surface plasmon resonance.

6. A method according to claim 2 wherein step d) comprises amplifying the SPNE by polymerase chain reaction (PCR).

7. A method according to claim 6 wherein step d) further comprises: ligating DNA encoding a SPNE to a DNA sequence encoding pIII, hepatitis B core antigen, or protein A to make a DNA encoding a recombinant fusion protein and expressing the recombinant fusion protein in a host.

8. A method according to claim 2 wherein the matrix is selected from the group consisting of: crossed-linked dextran, agarose, polyacrylamide, cellulose, silica, and poly (hydroxyethylmethacrylate).

9. A method according to claim 8 wherein the matrix is agarose.

10. A method of purifying antibodies which bind to a ligand, wherein the antibodies are present in an impure solution comprising:
    (1) selecting a ligand comprising the steps of:
        (a) preparing a phage expression library expressing a plurality of oligonucleotides comprising selected principle neutralization epitope (SPNE) candidate oligonucleotides, wherein the phage library has a complexity of approximately $40 \times 10^6$ different epitopes;
        (b) screening the phage library to determine which candidate oligonucleotide is a SPNE of the macromolecule by a process comprising attaching an essentially pure preparation of antibody to a solid-phase support and incubating the solid-phase supported antibody with the phage library to effect binding of SPNE to the solid-phase supported antibody;
        (c) determining association constants and dissociation constants of SPNE-antibody interactions using surface plasmon resonance and selecting a ligand from the SPNEs identified, wherein the ligand has an association constant within the range of about $1 \times 10^4$ to about $1\times10^6$ and a dissociation constant within the range of about $1\times10^{-2}$ to about $1\times10^{-5}$ with the antibodies;

(2) replicating the ligand to produce ligands;

(3) binding the ligands to a support matrix to produce bound ligands, wherein the matrix is selected from the group consisting of: cross-linked dextran, agarose, polyacrylamide, cellulose, silica, and poly(hydoxyethylmethacrylate);

(4) performing column chromatography on the impure solution containing the antibodies using a chromatography column comprising the bound ligands.

* * * * *